US011020334B2

(12) United States Patent
Kennedy et al.

(10) Patent No.: US 11,020,334 B2
(45) Date of Patent: Jun. 1, 2021

(54) COMPOUNDS, COMPOSITIONS AND USE THEREOF

(71) Applicant: Illustris Pharmaceuticals, Inc., Irvine, CA (US)

(72) Inventors: J. Phillip Kennedy, Newark, CA (US); Jacob M. Waugh, Irvine, CA (US)

(73) Assignee: Illustris Pharmaceuticals, Inc., Irvine, CA (US)

(*) Notice: Subject to any disclaimer, the term of this patent is extended or adjusted under 35 U.S.C. 154(b) by 0 days.

(21) Appl. No.: 16/487,067

(22) PCT Filed: Feb. 17, 2018

(86) PCT No.: PCT/US2018/018528
§ 371 (c)(1),
(2) Date: Aug. 19, 2019

(87) PCT Pub. No.: WO2018/152428
PCT Pub. Date: Aug. 23, 2018

(65) Prior Publication Data
US 2020/0054538 A1    Feb. 20, 2020

Related U.S. Application Data

(60) Provisional application No. 62/460,686, filed on Feb. 17, 2017.

(51) Int. Cl.
*A61K 8/36* (2006.01)
*A61K 8/34* (2006.01)
*A61K 8/49* (2006.01)
*A61Q 19/00* (2006.01)

(52) U.S. Cl.
CPC .............. *A61K 8/361* (2013.01); *A61K 8/342* (2013.01); *A61K 8/4926* (2013.01); *A61Q 19/001* (2013.01); *A61K 2800/40* (2013.01)

(58) Field of Classification Search
CPC ..... A61K 8/342; A61K 8/4926; A61Q 19/001
See application file for complete search history.

(56) References Cited

U.S. PATENT DOCUMENTS

| | | | |
|---|---|---|---|
| 2,502,868 A | 4/1950 | Martin et al. | |
| 3,637,717 A | 1/1972 | Vitale | |
| 4,190,594 A * | 2/1980 | Gander | A61K 8/671 424/59 |
| 4,216,224 A | 8/1980 | Von Scott et al. | |
| 5,086,060 A * | 2/1992 | Haley | C07D 277/66 514/294 |
| 7,015,225 B1 * | 3/2006 | Chen | C07D 213/02 514/252.01 |
| 7,173,062 B2 * | 2/2007 | Roh | A61K 8/671 514/529 |
| 7,550,510 B2 * | 6/2009 | Curley, Jr. | C07C 403/20 514/619 |
| 2012/0029198 A1 * | 2/2012 | Deng | A61Q 19/08 546/322 |
| 2016/0136076 A1 * | 5/2016 | Gaboardi | A61K 8/671 514/355 |

FOREIGN PATENT DOCUMENTS

| | | | | |
|---|---|---|---|---|
| CN | 1187193 A * | 7/1998 | | |
| DE | 4415204 A1 | 11/1995 | | |
| JP | 08073338 A * | 3/1996 | | |
| WO | WO1991001128 A1 * | 2/1991 | | |
| WO | WO 1995/016659 A1 | 6/1995 | | |
| WO | WO 2003/008457 A2 | 1/2003 | | |
| WO | WO-2014087307 A2 * | 6/2014 | ........... | A61K 47/542 |
| WO | WO 2014/204390 A1 | 12/2014 | | |
| WO | WO 2018/152428 A1 | 8/2018 | | |

OTHER PUBLICATIONS

Kim; Bioorganic & Medicinal Chemistry Letters 2009, 19, 508-512. (Year: 2009).*
Huttunen; Pharmacol Rev 2011,63, 750-771. (Year: 2011).*
International Search Report from International Application No. PCT/US2018/018528 dated May 11, 2018, application now published as International Publication No. WO2018/152428 on Aug. 23, 2018.

\* cited by examiner

*Primary Examiner* — Daniel R Carcanague
(74) *Attorney, Agent, or Firm* — Curtis Wadsworth

(57) ABSTRACT

This application relates to compounds prepared from cosmetically acceptable ingredients, methods of preparation thereof, and use thereof. Compounds are of formula (I) U—C—B, or salts thereof, wherein U, C and B are moieties of cosmetically acceptable ingredients U', C' and B'. In living tissues, the compounds can release at least one of U', C' and B'. The bond between C and U and/or between C and B is labile in living tissues. In particular, the compounds comprise moieties derived from salicylic acid, retinol and retinoic acid or nicotinic acid.

20 Claims, No Drawings

COMPOUNDS, COMPOSITIONS AND USE THEREOF

CROSS-REFERENCE TO RELATED APPLICATIONS

This application is a U.S. National Stage Application under 35 U.S.C. § 371 which claims the benefit of priority to International Patent Application No. PCT/US2018/018528, filed Feb. 17, 2018, which claims the benefit of priority to Provisional Patent Application No. 62/460,686 filed Feb. 17, 2017, each of which is hereby incorporated by reference in its entirety.

TECHNICAL FIELD

This application relates to compounds prepared from cosmetically acceptable ingredients, methods of preparation thereof, and use thereof.

BACKGROUND

Certain cosmetically acceptable ingredients, such as retinol, salicylic acid, and nicotinic acid which are some of the most highly utilized over the counter safe skin care actives, have limited topical penetration and stability in a single topical formulation. Cosmetically acceptable compounds with improved topical penetration and stability are therefore desired.

This application discloses compounds comprising moieties from cosmetically acceptable ingredients. Once in living tissues, the compounds disclosed herein can break apart and the individual cosmetically acceptable ingredient can be released. The compounds disclosed herein can display enhanced topical penetration for individual cosmetically acceptable ingredient, thereby exhibiting synergistic therapeutic effects of the cosmetically acceptable ingredients. The compounds disclosed herein can also eliminate incompatible formulation issues and skin irritation possibly associated with individual cosmetically acceptable ingredient.

SUMMARY

Disclosed is a compound of formula (I):
U—C—B (I), or a salt thereof, wherein U, C, and B are moieties of cosmetically acceptable ingredients U', C' and B', respectively, C is bonded to both B and U, and wherein the compound of formula (I) in living tissues can release at least one of U' C', and B', and wherein the bond between C and U and/or the bond between C and B are labile in living tissues.

Also disclosed is a cosmetic composition for making up and/or caring for the skin and/or lips comprising a compound of formula (I) and a cosmetically acceptable excipient.

DETAILED DESCRIPTION

I. Definitions

The singular forms "a," "an," and "the" include plural referents unless the context clearly dictates otherwise.

The dash ("—") in formulae (I) and (II) indicates a single bond. The dash that is not between two letters or symbols is used to indicate a point of attachment for a group. For example, —COO— is attached through the carbon atom and oxygen atom,

is attached through Y.

A "cosmetically acceptable ingredient" means an agent that is known to be active in improving a person's appearance-suitable for use in contact with the tissues of human beings and/or other mammals without excessive toxicity, irritation, allergic response, or other problem or complication, commensurate with a reasonable benefit/risk ratio. Improvement of the ingredient's penetration is expected to benefit a person's appearance with acceptable benefit/risk ratio.

A "cosmetically acceptable excipient" means an excipient that is useful in preparing a cosmetic composition that is generally safe, non-toxic and neither biologically nor otherwise undesirable.

The term "salt" as used herein embraces salts commonly used to form alkali metal salts of free acids and to form addition salts of free bases. The nature of the salt is not critical, provided that it is generally safe, non-toxic and neither biologically nor otherwise undesirable.

II. Compounds of Formula (I)

Provided is a compound of formula (I)
U—C—B (I), or a salt thereof, wherein U, C, and B are moieties of cosmetically acceptable ingredients U', C' and B', respectively, C is bonded to both B and U, and wherein the compound of formula (I) in living tissues can release at least one of U' C', and B', and wherein the bond between C and U and/or the bond between C and B are labile in living tissues.

In some embodiments, C is bonded to U through a carboxyl linkage (—COO—), amido linkage (—CONH—), or thiocarboxyl linkage (—COS— or —CSO).

In some embodiments, C is bonded to B through a carboxyl linkage (—COO—), amido linkage (—CONH—), or thiocarboxyl linkage (—COS— or —CSO).

Cosmetically Acceptable Ingredient C'

C' includes any cosmetically acceptable ingredient comprising two groups that are independently nucleophilic or electrophilic, which can react with cosmetically acceptable ingredient B' and U' to form the bond between C and B and the bond between C and U, respectively. In some embodiments, C' comprises two groups independently selected from OH, COOH, COSH, NH2, and SH. In some embodiments, C' comprises COOH and one group selected from OH, NH2, and SH. In some embodiments, C' comprises COSH and one group selected from OH, NH2, and SH. In some embodiments, C' comprises COOH and OH. In some embodiments, C' is salicylic acid. When C' is salicylic acid, C is

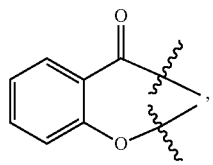 [SMILES: *Oc1ccccc1C(*)=O]

the squiggle line ⌇ marks the bond between C and B and the bond between C and U.

Cosmetically Acceptable Ingredient U'

U' includes any cosmetically acceptable ingredient comprising one group that is nucleophilic or electrophilic, which can react with C' to form the bond between C and U. In some embodiments, U' comprises one group selected from NH2, OH, SH, COSH, and COOH. In some embodiments, U' comprises one group selected from NH2, OH, and SH. In some embodiments, U' comprises one group selected from OH and COOH. In some embodiments, U' comprises OH. In some embodiments, U' is retinol. When U' is retinol, U is

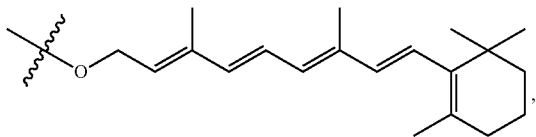 [SMILES: *OC/C=C(C)/C=C/C=C(C)/C=C/C1=C(C)CCCC1(C)C]

the squiggle line ⌇ marks the bond between C and U.

Cosmetically Acceptable Ingredient B'

B' includes any cosmetically acceptable ingredient comprising one group that is nucleophilic or electrophilic, which can react with C' to form the bond between C and B. In some embodiments, B' comprises one group selected from NH2, OH, SH, COSH, and COOH. In some embodiments, B' comprises one group selected from OH and COOH. In some embodiments, B' comprises COSH. In some embodiments, B' comprises COOH. In some embodiments, B' is nicotinic acid, isonicotinic acid, picolinic acid, or retinoic acid. In some embodiments, B' is nicotinic acid or retinoic acid. When B' is nicotinic acid, isonicotinic acid, picolinic acid, or retinoic acid, B is

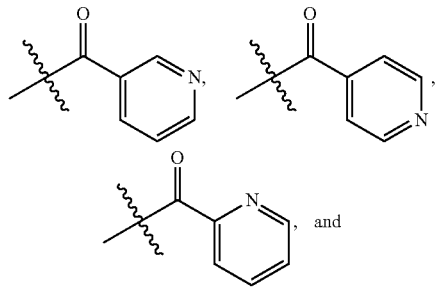

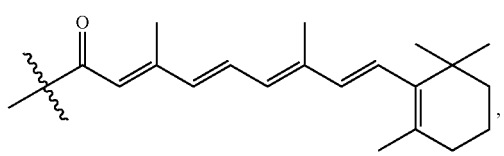

respectively, the squiggle line ⌇ marks the bond between C and B.

In some embodiments, the compound of formula (I) is a compound of formula (II)

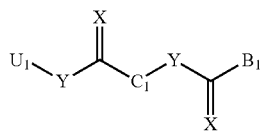

wherein

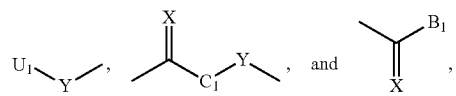

corresponding to U, C, and B, respectively, are moieties of cosmetically acceptable ingredients U', C' and B', respectively, X is independently O or S, and Y is independently O, S, or NH.

In some embodiments, X is O. In some embodiments, Y is O. In some embodiments, X and Y are O.

In some embodiments, the compound of formula (I) is a compound selected from

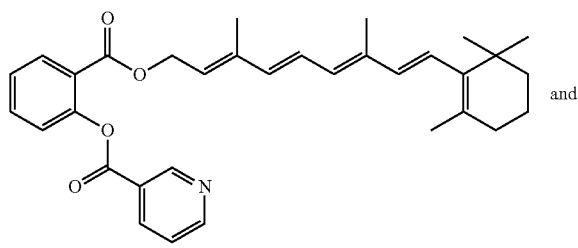

Compound 1 and

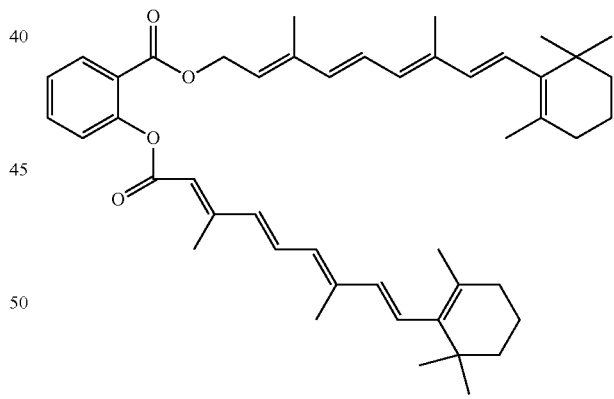

Compound 2

III. Cosmetic Compositions

In one aspect, a cosmetic composition for making up and/or caring for the skin and/or lips comprising a compound of formula (I) and a cosmetically acceptable excipient is provided.

The compositions are intended to be applied to the skin and/or lips of a subject, such as a person. The compositions can be formulated with any cosmetically acceptable excipient, and may be a liquid, semi-solid or solid composition. Cosmetically acceptable excipient suitable for topical administration of the compositions to the skin and/or lips are known to those skilled in the art and the compound of formula (I) can be included in an amount sufficient to provide a cosmetically useful result. Examples of excipients and various compositions are provided in the following paragraphs.

In one embodiment, the composition comprising the compound of formula (I) is a liquid. Liquid dosage forms for topical administration include emulsions, solutions and suspensions containing diluents commonly used in the art, such as alcohols, glycols, oils, water and the like.

The compositions may also include wetting agents, emulsifying and suspending agents.

The compositions may be in the form of solutions, suspensions, emulsions, ointments, lotions, gels, and the like. Emulsions of the form oil-in-water or water-in-oil are contemplated. Gels are formed by the entrapment of large amounts of aqueous or aqueous-alcoholic liquids in a network of polymers or of colloidal solid particles. Such polymers or colloids are typically present at concentrations of less than 10% w/w and are also referred to as gelling agents or thickening agents. Examples of suitable gelling agents include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, etc.

Creams and ointments may also be utilized. They are emulsions of oleaginous substances and water (i.e. the carrier). The cream may be a water-in-oil (w/o) in which an aqueous phase is dispersed in an oil phase, or an oil-in-water (o/w) which have an oil dispersed within an aqueous base. An ointment is also contemplated, and is typically more viscous than an oil-in-water cream. Traditional ointment bases (i.e. the carrier) include hydrocarbons (petrolatum, beeswax, etc.) vegetable oils, fatty alcohols (cholesterol, lanoilin, wool alcohol, stearyl alcohol, etc.) or silicones. Pastes are a type of ointment into which a high percentage of insoluble particulate solids have been added, up to 50% by weight. Insoluble solids such as starch, zinc oxide, calcium carbonate, or talc may be used.

Aerosols may also be utilized. The compound of formula (I) may be dissolved in a propellant and a co-solvent such ethanol, acetone, hexadecyl alcohol, etc. Foaming agents may be incorporated to produce a mousse.

Emollient or lubricating vehicles that help hydrate the skin can also be used. Examples of suitable bases or vehicles for preparing hydrating compositions for use with human skin are petrolatum, petrolatum plus volatile silicones, lanolin, cold cream (USP), and hydrophilic ointment (USP).

A wide variety of methods may be used for preparing the formulations described above. Broadly speaking, the formulations may be prepared by combining together the components of the formulation, as described herein, at a temperature and for a time sufficient to provide a pharmaceutically acceptable composition. The term "combining together", as used herein, means that all of the components of the compositions may be combined and mixed together at about the same time. The term "combining together" also means that the various components may be combined in one or more sequences to provide the desired product. The formulation can be prepared on a weight/weight (w/w) or a weight/volume (w/v) basis depending upon the form of the final dosage form.

The compositions comprise a weight fraction of the compound of formula (I), that may be dissolved, suspended, dispersed or otherwise mixed in a selected excipient, at an effective concentration such that the condition to be treated is relieved or ameliorated. Compositions that are in solution form and intended for topical administration may contain an amount a compound of formula (I) between about 0.01% w/w to about 50% w/w, or between about 0.01-25% w/w, with the balance of the composition being water, a suitable organic solvent or other suitable solvent or buffer. Compositions that are formulated as solutions, emulsions, or suspensions can be applied to the skin, or can be formulated as an aerosol or foam and applied to the skin as a spray-on. The aerosol compositions typically contain from 25% to 80% w/w, preferably from 30% to 50% w/w, of a suitable propellant.

Compositions of solid forms intended for topical application can be formulated as stick-type compositions intended for application to the lips or other parts of the body. Such compositions contain an effective amount of the compound of formula (I). The amount of the compound of formula (I) is typically from about 0.01% w/w to about 25% w/w or between about 0.01-15% w/w. The solid form of the composition may also contain from about 40% to 98% w/w, preferably from about 50% to 90% w/w, of carrier(s).

In addition, the compositions, and preparations containing the compositions, can also be coated on bandages, mixed with bioadhesives, or included in dressings. Thus, combinations of bandages, bioadhesives, dressings and other such materials and the compositions formulated as described herein are provided.

The compositions employed in the present methods can be administered topically to the area of interest as needed to provide a desired result. The result can be temporary or permanent, and can even be evident after a single dose of the composition.

The compositions may be packaged for use in a cosmetic setting or for retail distribution directly to the consumer (i.e., an article of manufacture or kit). Such articles will be labeled and packaged in a manner advising the customer how to use the product for therapy. These instructions may be in the form of pictures, written instructions, or a combination thereof. They may be printed on the side of the packaging, be an insert, or any other form of communication appropriate for the retail market.

IV. Use of the Compounds

In another aspect, a method for the treatment of acne, for improving visual appearance of the skin is provided. The method comprises administering a composition as described herein to the skin.

With regard to methods for cosmetic therapies, compositions as described herein can further comprise an agent having activity to improve visual or aesthetic appearance of the skin, such as an agent effective to reduce or diminish the appearance of fine lines and/or wrinkles on human facial skin or an agent effective to treating existing acne lesions, reducing redness associated with acne lesions and/or protecting from formation of acne lesions.

Exemplary agents are described below. "Improving the appearance of skin" and "improving the aesthetic appearance of skin" are used interchangeably herein to designate an aesthetic improvement in the appearance of skin. Representative improvements may include, but are not limited to, favorable characteristics and/or properties related skin thickness, elasticity, resiliency, smoothness, tone, texture, brightness, clarity, contour, firmness, tautness, and/or suppleness, and/or combinations thereof. In one embodiment, the terms intend the appearance of facial skin. Compounds useful for these compositions and for methods of improving appearance of skin are described.

Exemplary agent can be vitamin D compounds; vitamin K compounds, vitamin E compounds, or tocopherol, including tocopherol sorbate, tocopherol acetate, other esters of tocopherol; vitamin C compounds, including ascorbyl esters of fatty acids, and ascorbic acid derivatives, for example, ascorbyl glucoside, magnesium ascorbyl phosphate, sodium ascorbyl phosphate, and ascorbyl sorbate.

Oil Control Agents: In various embodiments the compositions may also comprise one or more compounds useful for regulating the production of skin oil, or sebum, and for improving the appearance of oily skin. Examples of suitable oil control agents include dehydroacetic acid, benzoyl peroxide, vitamin B3 compounds (for example, niacinamide), their isomers, esters, salts and derivatives, and mixtures thereof.

Other Skin Care Agents: The compositions in various embodiments may comprise N-acyl amino acid compounds. Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE (Registered trademark) from Seppic (France).

Skin care agents are disclosed in US Publication No. 2007/0020220A1, wherein the components/ingredients are incorporated herein by reference in their entirety. Other skin care agents include retinol, steroids, sunblock, salicylate, minocycline, antifungals, peptides, antibodies, lidocaine, A user topically applies the composition to a region on the skin that is in need of treatment. The composition is applied to the skin one or more times each day. In one embodiment, the composition is topically applied once daily for a period of at least 1 month, 2 months, 3 months, 4 months, 6 months, 8 months or 12 months. In one embodiment, the composition is applied at least once daily, or at least twice daily, or at least thrice daily.

EXAMPLES

The following examples are illustrative in nature and are in no way intended to be limiting.

Unless otherwise indicated, the reagents and reactants used in the experiments below are commercially available.

Example 1

Synthesis of Compound 1

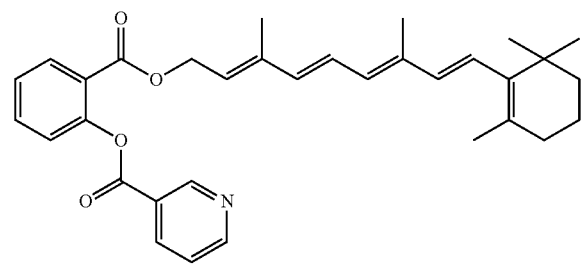 [SMILES: CC1=C(/C=C/C(C)=C/C=C/C(C)=C/COC(=O)c2ccccc2OC(=O)c2cccnc2)C(C)(C)CCC1]

Step 1: Synthesis of 2-(nicotinoyloxy)benzoic acid

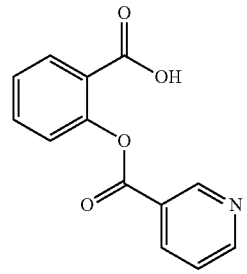 [SMILES: O=C(Oc1ccccc1C(=O)O)c1cccnc1]

To a 250 mL flask purged three times with Argon was added 3.2 g (18 mmol) of nicotinoyl chloride hydrochloride, and 45 mL of anhydrous pyridine. The resulting mixture was cooled to 0° C. A solution of 2.5 g (18 mmol) salicylic acid in 10 mL anhydrous pyridine was added to the mixture over 10 minutes. And the reaction mixture was stirred overnight. When reaction was complete, the reaction was quenched with 50 mL of distilled water and heated to boiling. White precipitates formed after the aqueous mixture was cooled. The white precipitates were collected and washed with cold distilled water three times to afford 2-(nicotinoyloxy)benzoic acid. The product was used in the next step without further purification.

Step 2: Synthesis of Compound 1

To a 250 mL flask purged three times with Argon was added 0.5 g (2 mmol) of 2-(nicotinoyloxy)benzoic acid, 24 mg (0.2 mmol) of dimethylaminopyridine, 0.59 g 92 mmol) of retinol and dissolved into 10 mL of anhydrous dimethylformamide:trimethylamine (9:1). To the resulting mixture was added 0.92 g (2.4 mmol) of HATU and the reaction was stirred overnight. After the reaction is complete, the reaction was quenched with 100 mL distilled water and extracted 3×100 mL with ethyl acetate. The combined ethyl acetate layer was dried with $MgSO_4$, followed by filtration and concentration. The obtained dark oil was purified via column chromatography utilizing Teledyne Isco Combiflash Rf+, (24 g column, 0→100% hexanes→ethyl acetate). The isolated material was then concentrated and dried under high vac to obtain 0.4 g (39%) of Compound 1.

Analytical data for Compound 1: $^1$H-NMR (400 MHz, $CDCl_3$): δ=9.36 (s, 1H), 8.78 (d, J=4.8 Hz, 1H), 8.42 (d, J=8 Hz, 1H), 8.34 (d, J=8.4 Hz, 1H), 8.03 (d, J=8.4 Hz, 1H), 7.70 (t, J=15.6 Hz, 1H), 7.53 (t, J=15.6 Hz, 1H), 7.45 (t, J=16.4 Hz, 1H), 6.57 (m, 1H), 6.11 (m, 4H), 5.47 (t, J=14.4 Hz, 1H), 4.84 (d, J=8 Hz, 2H), 1.96 (s, 3H), 1.79 (s, 3H), 1.72 (s, 3H), 1.57 (m, 6H), 1.03 (s, 6H). HRMS calcd for [M+H$^+$] 512.2795, found 512.2807.

Compound 2 can be prepared in a similar manner by replacing nicotinic acid with retinoic acid.

What is claimed is:

1. A compound selected from the group consisting of

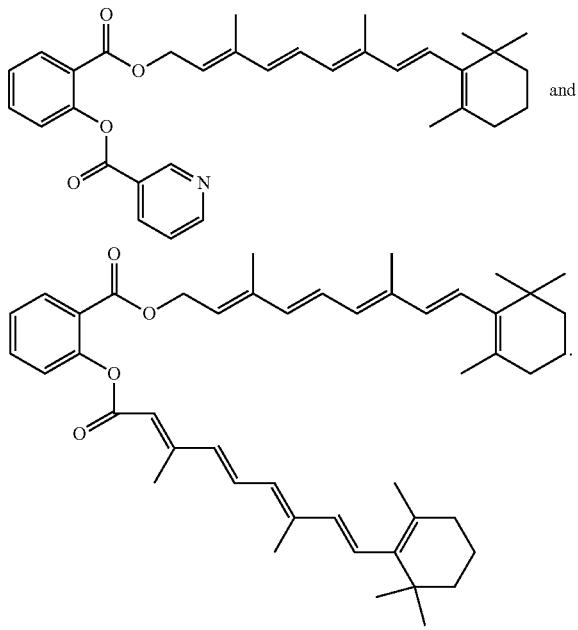

and.

2. A composition for making up and/or caring for the skin and/or lips comprising a compound of claim 1 and a cosmetically acceptable excipient.

3. The cosmetic composition of claim 2, wherein the composition is for caring for the skin.

4. The cosmetic composition of claim 2, wherein the composition is for caring for the lips.

5. The cosmetic of claim 2, wherein the composition is a liquid composition.

6. The composition of claim 5, wherein the liquid composition is for topical administration.

7. The composition of claim 2, wherein the composition is in the form of an emulsion, solution, suspension, cream, ointment, lotion, or gel.

8. The composition claim 7, further comprising a diluent.

9. The composition of claim 8, wherein the diluent is alcohol, glycol, oil, or water.

10. The composition claim 7, further comprising a wetting agent, an emulsifying agent, or a suspending agent.

11. The composition claim 7, wherein the liquid composition is in the form of an emulsion.

12. The composition of claim 11, wherein the emulsion is an oil-in-water or water-in-oil emulsion.

13. The composition of claim 7, wherein the liquid composition is a gel.

14. The composition of claim 13, wherein the gel comprises aqueous or aqueous-alcoholic liquids in a network of gelling agents or thickening agents.

15. The composition of 14, wherein the gel comprises less than about 10% w/w of the gelling or thickening agents.

16. The composition claim 15, wherein the gelling or thickening agent is carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, or carbomer.

17. The composition of claim 2, wherein the composition is in the form of an aerosol.

18. The composition of claim 17, wherein the aerosol is in the form of a mousse.

19. The composition of claim 2, further comprising an emollient or lubricating vehicle.

20. The composition of 19, wherein the emollient or lubricating vehicle is petrolatum, petrolatum plus volatile silicones, lanolin, cold cream (USP), or hydrophilic ointment (USP).

* * * * *